United States Patent [19]
Herzog

[11] Patent Number: 6,114,573
[45] Date of Patent: Sep. 5, 2000

[54] CATALYST, PROCESS FOR PRODUCING THE CATALYST AND PROCESS FOR PREPARING VINYL ACETATE USING THE CATALYST

[75] Inventor: Bernhard Herzog, Oberhausen, Germany

[73] Assignee: Celanese GmbH, Germany

[21] Appl. No.: 09/324,819

[22] Filed: Jun. 2, 1999

Related U.S. Application Data

[62] Division of application No. 09/203,688, Dec. 2, 1998, Pat. No. 5,968,860.

[30] Foreign Application Priority Data

Dec. 11, 1997 [DE] Germany ............... 197 54 992

[51] Int. Cl.[7] ............... C07C 67/02; B01J 19/12
[52] U.S. Cl. ...................... 560/261; 422/186.29
[58] Field of Search ............ 562/261; 422/186.29

*Primary Examiner*—Gary Geist
*Assistant Examiner*—Robert W. Deenie
*Attorney, Agent, or Firm*—Bierman, Muserlian and Lucas

[57] ABSTRACT

A process for the production of a catalyst for preparing vinyl acetate in the gas phase from ethylene, acetic acid and oxygen or oxygen-containing gases which catalyst comprises palladium and/or its compounds, gold and/or its compounds and also alkali metal compounds on a particulate, porous support obtained by a) impregnating the support with soluble palladium and gold compounds, b) converting the soluble palladium and gold compounds into insoluble palladium and gold compounds by addition of an alkaline solution to the support.

c) reducing the insoluble palladium and gold compounds on the support with a reducing agent in the liquid or gaseous phase, d) impregnating the support with at least one soluble alkali metal compound and e) finally drying the support at a maximum of 150° C., wherein the catalyst is irradiated with microwaves before, during or after one of process steps a) to e).

3 Claims, No Drawings

6,114,573

CATALYST, PROCESS FOR PRODUCING THE CATALYST AND PROCESS FOR PREPARING VINYL ACETATE USING THE CATALYST

PRIOR APPLICATION

This application is a division of U.S. patent application Ser. No. 09/203,688 filed Dec. 2, 1998, now U.S. Pat. No. 5,968,860, issued Oct. 19, 1999.

A catalyst comprising palladium and/or its compounds, gold and/or its compounds and also at least one alkali metal compound, a process for producing it and its use for preparing vinyl acetate in the gas phase from acetic acid, ethylene and oxygen or oxygen-containing gases.

STATE OF THE ART

It is known from the prior art that vinyl acetate can be prepared in the gas phase from ethylene, oxygen and acetic acid in the presence of catalysts which comprise palladium, gold and alkali metal compounds on a porous support material such as silicon dioxide.

The distribution of the noble metals on the support material is of particular importance for the activity and selectivity of these catalysts. Since the reactants in the reaction to be catalyzed cannot readily diffuse into the intermediate or inner regions of the porous support material, the reaction takes place essentially only on the outermost or surface regions of the catalyst. Thus, the metal components present in the interior or in the intermediate regions of the support do not contribute significantly to the reaction mechanism, which leads to a reduction in productivity of the catalyst based on the weight of the noble metals.

In the development of effective catalysts for vinyl acetate production, efforts have therefore been directed at providing catalysts in which the catalytically active noble metals are present in a shell on the support particles while the core of the support particles is largely free of noble metals. Such shell catalysts can in principle be produced by impregnation of the support material with soluble noble metal compounds, subsequent precipitation of insoluble noble metal compounds on the support by addition of alkaline compounds and final reduction to the noble metals.

U.S. Pat. No. 4,048,096 describes a process for producing a palladium-, gold- and potassium-containing catalyst for vinyl acetate production. The catalyst support is first impregnated with a solution comprising a mixture of the dissolved palladium and gold salts. It is essential to that invention that the solution has the same volume as the pores of the support material in the dry state. During the impregnation step, the support particles are kept in motion in a rotating vessel. Without prior drying of the impregnated support, the noble metal salts on the support particles are subsequently converted into insoluble compounds by addition of alkalis and are thus fixed to the support particles. The palladium and gold compounds are reduced to the corresponding metals by a final treatment with a reducing agent. Application of an alkali metal compound in a further impregnation step gives a catalyst which has the desired shell structure and comprises palladium and gold in a thickness of 0.5 mm on the surface of the support material.

U.S. Pat. No. 3,775,342 also describes the production of a palladium-, gold- and potassium-containing catalyst for vinyl acetate production. In this process, the support material is treated in any order with two solutions of which one comprises the dissolved palladium and gold salts and the other an alkaline substance. After treatment with the first solution, the support is dried in an intermediate step before being brought into contact with the second solution. The volume of both solutions corresponds to the pore volume of the support material.

Furthermore, U.S. Pat. No. 5,332,710 discloses the production of a catalyst for preparing vinyl acetate, in which the insoluble noble metal salts are likewise precipitated on the support particles by addition of alkalis. For this purpose, the support particles are immersed in the alkaline solution and are subjected to rotary motion from the commencement of the precipitation for at least half an hour in a drum. This process is known as "rotation-immersion."

In the preparation of vinyl acetate, the catalysts produced as described in the above-mentioned process frequently lead to undesirably high formation of degradation products and by-products, e.g. carbon dioxide, thus adversely affecting activity and selectivity of the overall reaction.

OBJECTS OF THE INVENTION

Since vinyl acetate is a volume product produced on a large industrial scale, it is an object of the invention to provide a catalyst which has a further improved activity and selectivity in the preparation of vinyl acetate in the gas phase.

This and other objects and advantages of the invention will become obvious from the following detailed description.

THE INVENTION

The invention provides a process for producing a catalyst for the preparation of vinyl acetate in the gas phase from ethylene, acetic acid and oxygen or oxygen-containing gases, which catalyst comprises palladium and/or its compounds, gold and/or its compounds and also alkali metal compounds on a particulate, porous support produced by a) impregnating the support with soluble palladium and gold compounds, b) converting the soluble palladium and gold compounds into insoluble palladium and gold compounds by addition of an alkaline solution to the support, c) reducing the insoluble palladium and gold compounds on the support with a reducing agent in the liquid or gaseous phase, d) impregnating the support with at least one soluble alkali metal compound and e) finally drying the support at a maximum of 150° C., the improvement comprising the catalyst is irradiated with microwaves during, before or after one of process steps a) to e).

The invention also provides a catalyst for preparing vinyl acetate in the gas phase from ethylene, acetic acid and oxygen or oxygen-containing gases, which comprises palladium and/or its compound, gold and/or its compounds and also alkali metal compounds on a particulate, porous support obtained by the above-described process.

The invention further provides a process for preparing vinyl acetate in the gas phase from ethylene, acetic acid and oxygen and/or oxygen-containing gases in the presence of a catalyst obtained by the above-described process. In the preparation of vinyl acetate, the catalysts of the invention surprisingly lead both to an improved activity and to a higher selectivity of the reaction, but also makes possible a higher space-time yield.

The support particles of the catalyst of the invention can have any geometric shape, for example spheres, pellets, cylinders, rings or stars with a regular or irregular configuration. The dimensions of the support particles, i.e. the diameter or the length and thickness are generally from 1 to 10 mm, particularly from 3 to 9 mm. Preference is given to using spherical support particles having a diameter of from 4 to 8 mm.

Supports which can be used are the known inert support materials such as silica, aluminum oxide, alumino-silicates, silicates, titanium oxide, zirconium oxide, titanates, silicon carbide and carbon. Other suitable support materials are the pyrogenic silicas obtained by flame hydrolysis of silicon tetrachloride or the pyrogenic $SiO_2$—$M_xO_y$ mixture obtained by flame hydrolysis of silicon tetrachloride and another metal chloride such as aluminum chloride (U.S. Pat. No. 3,939,199 and EP-A-0 723 810). Preference is given to using silica ($SiO_2$), baddeleyite ($ZrO_2$) and $SiO_2$—$Al_2O_3$ mixtures as support material. In the case of the pyrogenic support materials, the pressed bodies described in DE-A-38 03 895 and DE-A-39 12 504 are particularly suitable.

To be suitable as support material, it is particularly important that the material retains its mechanical strength under the reaction conditions of the catalytic process for preparing vinyl acetate, particularly in the presence of acetic acid.

Particularly suitable supports are those of the above-mentioned type having a specific surface area of from 50 to 400 $m^2$/g (measured by the BET method) and a mean pore radius of from 50 to 2000 Å (measured by means of mercury porosimetry).

In step a) of the process of the invention, the impregnation step, the support particles are impregnated with the dissolved palladium and gold compounds. Suitable palladium and gold compounds are all salts and complexes which are soluble in the solvents described below, can be precipitated as hydroxide or oxide and in the finished catalyst, possibly after a washing step, leave no materials which impair performance of the catalyst.

Examples of suitable palladium compounds are palladium (II) chloride, sodium and potassium chloropalladate(II), palladium(II) nitrate, nitrite, sulfate, oxalate, acetylacetonate or acetoacetate and hydrated palladium(II) oxide. It is also possible to use palladium salts of aliphatic monocarboxylic acids of 2 to 5 carbon atoms, preferably palladium(II) acetate. Gold(III) chloride, gold(III) acetate, tetrachloroauric (III) acid and its alkali metal salts can be used as soluble gold compounds. In general, these compounds are used in such amounts that the finished catalyst comprises from 2 to 14 g/l, preferably from 4 to 8 g/l, of palladium and from 1 to 8 g/l, preferably from 2 to 5 g/l, of gold.

Suitable solvents for the palladium and gold compounds and also for the alkali metal compounds to be applied in step d) are all compounds in which the salts chosen are soluble and which are easy to remove again in an optional drying step after the impregnation. Particularly suitable solvents are water and unsubstituted carboxylic acids of 2 to 10 carbon atoms, e.g. acetic acid, propionic acid, n- and iso-butyric acids and n- and iso-valeric acids. Owing to its favorable physical properties and also for economic reasons, the preferred carboxylic acid is acetic acid.

It is advantageous to use an additional solvent when the palladium and gold compounds are not sufficiently soluble in the carboxylic acid used. Thus, for example, palladium(II) chloride dissolves significantly better in aqueous acetic acid than in glacial acetic acid. Suitable additional solvents are those which are inert and at the same time are miscible with the carboxylic acid, e.g. water, ethers such as tetrahydrofuran or dioxane and hydrocarbons such as benzene.

In the impregnation of the support material, it is possible to use a plurality of salts of each of the metals to be applied, but preference is given to using only one salt per metal.

The impregnation of the support material with the soluble palladium and gold compounds in step a) can be carried out using a solution which simultaneously comprises all soluble palladium and gold compounds. Here, the support material can be impregnated once or a plurality of times with this solution. Since the amount of palladium and gold compounds used should be identical in single and multiple impregnation, the total volume of the solution should be divided appropriately in the case of multiple impregnation. Preference is given to a single impregnation with the total volume of the solution.

In an alternative embodiment, the impregnation of the support material can also be carried out using two separate solutions of which one contains the palladium compounds and the other contains the gold compounds. In this case, the two solutions can be brought into contact with the support material either simultaneously or else in any order. In the latter case, the support has to be dried after impregnation with the first solution.

For effective impregnation, the total volume of the noble metal salt solution or of the two noble metal salt solutions should be about 90–100%, preferably 95–100% and in particular 98–99%, of the pore volume of the support material in the dry state. In practice, it is also possible to cover the support particles with an excess of the noble metal salt solution and subsequently to pour away or filter off the excess solution. However, preference is given to adding only the above-described amount of solution corresponding approximately to the pore volume of the catalyst support.

It has been found to be advantageous to keep the support particles in motion during the impregnation to achieve intimate mixing. This can be done by means of a rotating or shaken flask or a mixing drum. The rotational speed or in general terms, the intensity of the motion should be sufficient to achieve complete wetting of the support particles with the impregnation solution but must not be so great that appreciable abrasion of the support material occurs.

If desired, the impregnated support material is dried at temperatures of at most 150° C., preferably 80–150° C. and more preferably 100–150° C. This drying procedure can be carried out, for example, in a stream of hot air in a fan-forced drier or in a drying oven in a stream of inert gas, particularly a stream of nitrogen or carbon dioxide. Drying is carried out at atmospheric pressure or under reduced pressure, preferably 0.01–0.08 MPa.

In step b), the fixing step, the soluble palladium and gold compounds present on the support particles are converted into insoluble compounds with an alkaline solution and are thus fixed to the support. It is assumed that the insoluble compounds are the hydroxides and/or oxides of the noble metals.

Suitable alkaline solutions are all solutions which are able to convert the soluble palladium and gold compounds into insoluble compounds. Example of alkaline reagents which can be used are alkali metal hydroxides, alkali metal silicates and alkali metal carbonates. Preference is given to an aqueous solution of the alkali metal hydroxides, particularly of potassium or sodium hydroxide. Solutions containing boron compounds can also be used as alkaline solutions. Here, aqueous solutions of sodium tetraborate decahydrate (borax), potassium tetraborate or mixtures of alkali metal hydroxide and boric acid are particularly suitable. The alkaline solution can have buffer properties.

The amount of alkaline compound present in the aqueous solution is advantageously selected so that it is at least sufficient for the stoichiometric reaction with the soluble palladium and gold compounds applied. However, it is also possible to use an excess of the alkaline compound, usually 1–10 times the stoichiometrically required amount.

Two methods I and II which are suitable for carrying out the fixing step b) and can be employed in the production of the catalyst of the invention are described below.

In method I, the support material impregnated in step a) is placed for a sufficient time in an alkaline solution whose concentration is such that the desired, insoluble noble metal compounds are precipitated. In addition, the volume of the alkaline solution is selected so that it is sufficient to completely cover and immerse the impregnated support particles. Furthermore, the impregnated support particles immersed in the alkaline solution are subjected to rotary motion commencing with the precipitation of the insoluble palladium and gold compounds for at least half an hour, preferably one hour and at most up to 4 hours. This fixing method is known as "rotation-immersion" and is described in detail in U.S. Pat. No. 5,332,710, which is hereby incorporated by reference.

If method II described below is employed for fixing the palladium and gold compounds to the support particles, the support which has been impregnated in step a) should be dried before the fixing step b).

In method II, the fixing step b) comprises at least two separate stages of treatment with the alkaline fixing solution. In the first fixing stage, the impregnated and then dried support is brought into contact with the alkaline fixing solution. The volume of this first fixing solution corresponds to the pore volume and thus the absorptive capacity of the support material in the dry state. The amount of alkaline compounds present therein should be such that the molar ratio of alkali metal from the alkaline compound to anions from the soluble metal salt is in the range from 0.7:1 to 2:1. For absorption on the support particles, the alkaline fixing solution is poured onto the support particles and they are then left to stand for up to 24 hours, preferably 2–8 hours.

In this method II, the second fixing stage can be carried out in two variants A) and B). In both variants, the molar ratio of the alkali metal from the alkaline compound to the anion from the metal salt is from about 0.2:1 to 2:1 in the fixing solution.

In variant A) of method II, the undried support particles are brought into contact with the second fixing solution whose volume should at least just cover the supports. For absorption on the support particles, the alkaline fixing solution is poured onto the support particles and they are then left to stand for up to 16 hours, but at least 2 hours and preferably at least 4 hours.

In variant B), the support material after contact with the first fixing solution is, in the second step, treated by the rotation-immersion process of U.S. Pat. No. 5,332,710. Here, the support material is immersed in the alkaline fixing solution of the second step and at the same time subjected to rotary motion. This rotation should continue for at least half an hour, preferably one hour and at most up to 4 hours.

Regardless of whether variant A) or B) is employed, the treatment in the second fixing step can be equivalent to the treatment in the first stage in that a fixing solution of the same concentration is used and the volume of the second fixing solution likewise corresponds to the pore volume and thus the absorptive capacity of the support material in the dry state. The total molar ratio of alkali metal to anion from the metal salt for both fixing stages together is preferably in the range from 1.1:1 to 3.3:1.

After the fixing step of method I or the last fixing step of method II, the supports can be washed with water, preferably with distilled water, to remove any interfering anions, e.g. chlorides, which originate from the impregnation step, have been set free by the precipitation of the noble metals and are still present on the support material. This washing procedure also removes any excess of alkaline compound which may still be present.

If desired the impregnated material is dried at temperatures of at most 150° C., preferably 80–150° C. and more preferably 100–150° C. This drying procedure can be carried out, for example, in a stream of hot air in a fan-forced drier or else in a drying oven in a stream of inert gas, particularly in a stream of nitrogen or carbon dioxide. Drying is carried out at atmospheric pressure or under reduced pressure, preferably 0.01–0.08 MPa.

Such a drying procedure is advantageous at this point particularly when the reduction step c) described below is carried out in the gas phase. In contrast, prior drying is not necessary if the reduction is carried out in the liquid phase.

In step c), the support together with the insoluble palladium and gold compounds deposited thereon is treated with a reducing agent to convert the precipitated palladium and gold compounds into the metallic form. This reduction can be carried out in the liquid phase at a temperature of 0–90° C., preferably 15–25° C.

The reducing agent used here is, for example, hydrazine, formic acid or an alkali metal borohydride, preferably sodium borohydride. As an alternative, it is also possible to carry out the reduction in the gas phase using hydrogen, ethylene, propylene, isobutylene, butylene or other olefins as reducing agent. In this case, it is advantageous to carry out the reduction at an increased temperature of 40–260° C., preferably 70–200° C. It is also advantageous to dilute the reducing agent with an inert gas. The inert gas used can be, for example, nitrogen, carbon dioxide or a noble gas. Such a reducing agent/inert gas mixture usually contains 0.01–50% by volume, preferably 0.5–20% by volume, of reducing agent.

Regardless of whether the reduction is carried out in the liquid or gas phase, the reducing agent should be added in an excess, based on the catalyst to be reduced, so as to ensure that all the insoluble noble metal compound is converted into the metallic form.

After the reduction, the support particles can be washed once again or a plurality of times, preferably with distilled water, to remove interfering anions, e.g. chlorides, and residues of the alkaline solution used. The washing procedure can also serve to remove residues of the reducing agent from step c).

Subsequently, the catalyst is dried again under drying conditions which should be similar to those of a drying step after the fixing step b).

Finally, the addition of at least one alkali metal compound is necessary. The catalyst is therefore impregnated with an aqueous solution of an alkali metal compound in step d). Alkali metal compounds which can be used are sodium, potassium, rubidium or cesium compounds; preference is given to potassium compounds.

Suitable anions of these alkali metal compounds are, in particular, carboxylates, especially acetates or propionates. Particular preference is given to using potassium acetate. However, it is also possible to use compounds which liberate alkali metal acetates under the reaction conditions, i.e. the alkali metal hydroxides, oxides or carbonates when acetic acid is used as solvent. This impregnation is carried out, in principle, in the same way as the impregnation of the support material in step a). The solvents which can be used are subject to the same conditions and definitions as in the case of the solutions in impregnation step a). The alkali metal compound is used in such an amount that the catalyst after the drying step described below contains 0.1–10% by weight of alkali metal, preferably 1–4% by weight of alkali metal, in particular potassium, based on the total mass of the catalyst.

Finally, the catalyst is, in step e), dried at temperatures of at most 150° C., preferably 80–150° C. and more preferably 100–150° C. This drying procedure can be carried out, for example, in a stream of hot air in a fan-forced drier or in a drying oven in a stream of inert gas, particularly in a stream of nitrogen or carbon dioxide. Drying is carried out at atmospheric pressure or under reduced pressure, preferably 0.01–0.08 MPa.

In the above-described process comprising the steps a) to e), the catalyst is irradiated with microwaves before, during or after one of the steps a) to e).

One embodiment of the process of the invention comprises exposing the untreated catalyst support to microwaves irradiation before the impregnation step a). As an alternative thereto, the catalyst can be irradiated with the microwaves after the impregnation step a) and before the fixing step b). It is also possible to use the microwaved during the reduction step c), particularly when the reduction is carried out in the gas phase. Furthermore, the catalyst can also be irradiated with microwaves and heated in this way only after step e).

The catalyst is usually irradiated at a radiation frequence of from 300 MHz to 30 GHz; irradiation is preferably carried at 2.45 GHz. A microwave power of 10–2000 W, preferably 180–900 W, in particular 300–600 W, and an irradiation time of up to 10 hours, preferably 1–60 min, more preferably 5–15 min, have been found to be useful.

The catalyst obtained by steps a) to e) of the process of the invention and the treatment with the microwave irradiation essential to the invention comprises, based on the total mass of the catalyst, 0.2–2.5% by weight, preferably 0.6–1.5% by weight, of palladium, 0.2–2.5% by weight, preferably 0.3–1.0% by weight, of gold and 0.1–10% by weight of alkali metal, preferably 1.0–4.0% by weight of alkali metal, in particular potassium.

Vinyl acetate is prepared by passing acetic acid, ethylene and oxygen or oxygen-containing gases at temperatures of from 100 to 220° C., preferably from 120 to 200° C., and pressures of from 0.1 to 2.5 MPa, preferably from 0.1 to 2 MPa, over the catalyst of the invention. Unreacted components can be circulated. In some cases, dilution with inert gases such as nitrogen or carbon dioxide is also advantageous. Carbon dioxide is particularly suitable for dilution in a circulation mode of operation since it is in any case formed during the reaction.

It has been found to be useful to carry out the preparation of the vinyl acetate in a stirred reactor, a Berty reactor, in circulation mode in the gas phase at a constant oxygen conversion of about 45%. The reactor is first charged with the catalyst. Subsequently, a measured amount of acetic acid and also ethylene and oxygen diluted with nitrogen is introduced and the temperature is increased to the desired value using a heating mantle. The reaction is usually stopped after about 18 hours, as long as it has been possible to set a temperature at which the oxygen conversion is constant at 45%. The composition of the product mixture is determined by means of gas chromatography.

The higher selectivity and greater space-time yield achievable using the catalysts of the invention can in practice be utilized in two ways:

Firstly, to produce a larger amount of vinyl acetate per unit volume and unit time in existing plants while retaining all other reaction conditions. Owing to the higher selectivity, the product mixture taken from the reactor has a higher proportion of vinyl acetate and contains less by-products, particularly carbon dioxide. In this way, the work-up, i.e. the isolation of the vinyl acetate, is made easier because, for example, the amount of carbon dioxide to be separated off is lower and accordingly the loss of entrained ethylene associated with the removal of carbon dioxide drops. This leads to a saving in starting material. The principles of the work-up of the product mixture after the preparation of vinyl acetate are described, for example, in EP-A-0 423 658.

The second possible way of utilizing the improved properties of the catalysts of the invention is to lower the reaction temperature in the preparation of vinyl acetate while maintaining the same space-time yield. A lower reaction temperature in turn has a positive effect on the total operational life of the catalyst.

In the following examples, there are described several preferred embodiments to illustrate the invention. However, it should be understood that the invention is not intended to be limited to the specific embodiments.

EXAMPLES 1 and 2

The catalyst support used was a spherical silicon dioxide from Sudchemie AG having a diameter of 7 mm and a pore volume of 324 ml of water/g. 250 ml of the support were impregnated with an aqueous solution of sodium tetrachloropalladate and sodium tetrachloroaurate. The supports were subsequently dried in hot air at a temperature which did not exceed 100° C. The supports treated in this way were impregnated with an aqueous sodium hydroxide solution and the volume of the sodium hydroxide solution was equal to the dry absorptive capacity of the supports. After the first stage, the support which had been treated with base was allowed to stand for 4 hours and was subsequently poured into a second sodium hydroxide solution. The volume of this second sodium hydroxide solution was also equal to the dry absorptive capacity of the support material. After the second treatment, the material which had been treated with base was allowed to stand for an additional time of about 16 hours. After the fixing procedure, the material which had been treated with base was washed thoroughly with distilled water.

The catalyst was dried in a constant stream of nitrogen at a temperature of not more than 150° C. and the dried catalysts were subsequently reduced with ethylene at a temperature of 150° C. The reducing gas comprised 5% of ethylene in nitrogen and was passed over the catalysts for 5 hours at atmospheric pressure. The reduced catalyst was impregnated with an aqueous solution of 10 g of potassium acetate and having a volume which corresponded to the absorptive capacity of the support. The catalysts were dried at a temperature of not more than 150° C. Subsequently, the catalyst was irradiated at room temperature with mnicrowaves having a frequency of 2.45 GHz at a microwave power of 600 W for 10 minutes.

Comparative Example

The catalyst was produced as described in Example 1 but the irridiation with microwaves was omitted after the last drying step.

Preparation of Vinyl Acetate

The catalysts produced in Examples 1 and 2 and in the Comparative Example were used to prepare vinyl acetate in the gas phase from ethylene, acetic acid and oxygen-containing gases in a Berty reactor. The experimental results are summarized in Table i below.

Table 1

Preparation of vinyl acetate using the catalysts of Examples 1 and 2 and the Comparative Example

| Example | Space-time yield (g V A M/ $L_{catalyst} \cdot h$) | $CO_2$ selectivity (% based on the amount of ethylene reacted) |
|---|---|---|
| 1 | 746 | 8.8 |
| 2 | 742 | 8.9 |
| comparative | 715 | 9.5 |

Various modifications of the processes and catalysts may be made without departing from the spirit or scope thereof and it is to be understood that the invention is intended to be limited only as defined in the appended claims.

What is claimed is:

1. In a process for preparing vinyl acetate in the gas phase from ethylene, acetic acid and oxygen and/or oxygen-containing gases in the presence of a catalyst, the improvement comprising using a supported catalyst comprising palladium and/or a compound thereof, gold or a compound thereof and also alkali metal compounds on a particulate, porous support, said catalyst comprising, based on the total mass of the catalyst, 0.2–2.5% by weight of palladium, 0.2–2.5% by weight of gold and 0.1–10% by weight of alkali metal and which catalyst is produced by a) impregnating the support with a solution of soluble palladium and gold compounds, b) converting the soluble palladium and gold compounds into insoluble palladium and gold compounds by addition of an alkaline solution to the support, c) reducing the insoluble palladium and gold compounds on the support with a reducing agent in the liquid or gaseous phase, d) impregnating the palladium and gold containing support with at least one soluble alkali metal compound and e) finally drying the impregnated support at a maximum of 150° C.

wherein the catalyst is irradiated with microwaves before, during or after one of process steps a) to e) as the catalyst.

2. The process of claim 1 carried out at temperatures of from 100 to 220° C. and pressures of from 0.1 to 2.5 MPa.

3. The process of claim 1 wherein the temperature is 120 to 200° C. and the pressure is 0.1 to 2 MPa.

* * * * *